US012329863B2

(12) United States Patent
Nguyen et al.

(10) Patent No.: US 12,329,863 B2
(45) Date of Patent: Jun. 17, 2025

(54) WOUND DRESSING ARTICLES AND METHOD OF MANUFACTURING THE SAME

(71) Applicants: Hiep Thi Nguyen, Ho Chi Minh (VN); Toi Van Vo, Arlington, MA (US)

(72) Inventors: Hiep Thi Nguyen, Ho Chi Minh (VN); Toi Van Vo, Arlington, MA (US)

(73) Assignee: Vietnam National University Ho Chi Minh City, Ho Chi Minh (VN)

( * ) Notice: Subject to any disclaimer, the term of this patent is extended or adjusted under 35 U.S.C. 154(b) by 379 days.

(21) Appl. No.: 17/814,529

(22) Filed: Jul. 24, 2022

(65) Prior Publication Data

US 2023/0118969 A1    Apr. 20, 2023

(51) Int. Cl.
| | |
|---|---|
| A61L 15/18 | (2006.01) |
| A61F 13/02 | (2024.01) |
| A61L 15/22 | (2006.01) |
| A61L 15/44 | (2006.01) |
| D01D 5/00 | (2006.01) |
| D01F 6/30 | (2006.01) |
| D01F 6/62 | (2006.01) |

(52) U.S. Cl.
CPC .......... *A61L 15/18* (2013.01); *A61F 13/0289* (2013.01); *A61L 15/225* (2013.01); *A61L 15/44* (2013.01); *D01D 5/0007* (2013.01); *D01F 6/30* (2013.01); *D01F 6/625* (2013.01); *A61L 2300/404* (2013.01); *D10B 2509/022* (2013.01)

(58) Field of Classification Search
CPC ........ A61L 15/18; A61L 15/225; A61L 15/44; A61L 2300/404; A61L 26/0019; A61L 15/26; A61L 15/32; A61L 15/46; A61L 26/0038; A61L 26/0052; A61L 26/0066; A61L 26/008; A61L 2300/104; A61F 13/0289; A61F 13/022; A61F 13/00063; D01D 5/0007; D01D 5/0038; D01F 6/30; D01F 6/625; D01F 6/66; D01F 6/92; D10B 2509/022

See application file for complete search history.

(56) References Cited

U.S. PATENT DOCUMENTS

| | | | | |
|---|---|---|---|---|
| 2012/0071807 A1* | 3/2012 | McClure, Jr. | ........... | A61L 15/46 |
| | | | | 602/48 |
| 2013/0231623 A1* | 9/2013 | Richard | ............ | A61F 13/00987 |
| | | | | 604/372 |

FOREIGN PATENT DOCUMENTS

| | | | | | |
|---|---|---|---|---|---|
| CN | 1850288 | A | * | 10/2006 | ............. A61F 13/02 |
| CN | 113633813 | A | * | 11/2021 | |
| CN | 113813107 | A | * | 12/2021 | |
| EP | 3287149 | A1 | * | 2/2018 | ............. A61L 15/26 |
| JP | 2022523780 | A | * | 2/2019 | |
| KR | 20100021108 | A | * | 8/2008 | |

(Continued)

Primary Examiner — Tarla R Patel (57) ABSTRACT

The present invention provides a medical dressing article and a method of manufacturing the same, which comprises: (a) a first layer comprised of polycaprocaptone fibers having a PCL fiber diameter of 0.5 μm and 2.9 μm; (b) a second layer, deposited directly on the first layer, including a mixture of polycaprolactone and poloxamer fibers (PCL and POX fibers) wherein a PCL and POX fiber diameter is between 0.1 μm and 4 μm; and (c) a third layer, deposited directly on the second layer, further comprising a mixture of gelatin and silver nitrate ($AgNO_3$).

20 Claims, 9 Drawing Sheets

(56) References Cited

FOREIGN PATENT DOCUMENTS

WO     WO-2020159946 A1 *   8/2020   ....... A61F 13/00017
WO     WO-2021137776 A1 *   7/2021   ....... A61F 13/00017

* cited by examiner

WOUND DRESSING ARTICLES AND METHOD OF MANUFACTURING THE SAME

FIELD OF THE INVENTION

The present invention relates generally to the field of medical devices. More specifically, the present invention relates to medical wound dressing articles having antimicrobial and non-adherent properties.

BACKGROUND ART

Currently the methods of making gauzes and biofilms for wound care products by electric field spinning are quite common. These prior art methods are described below:

A Chinese patent No. CN106730018 B ("30018 patent") is about a composite film consisted of a hydrophobic non-adherent layer, a hydrophilic frame layer, and a transition layer between the non-adherent layer and the hydrophilic frame layer. These layers are made up of fibers containing polymers such as polyurethanes, polyglycolides, polylactides, polycaprolactones (PCL), polydioxanons, etc. and biological materials such as collagen, chitosan, sodium alginate, fibroin, etc. In addition, the hydrophilic frame contains active ingredients such as chondroitin sulfate, vitamin C, epidermal growth factor, etc. The 30018 patent describes a method of fabricating composites by electric field spinning.

The international gazette patent number WO2013/017719 A1 ("the '719 patent) discloses a laminated film consisting of an inner layer containing polylactic acid polarizers, polyhydroxyalkanoates (PHA), polycarpolacton (PCL), etc. and at least one coating containing hydrophobic and/or water-resistant substances such as polyolefin, polyurethanes, styrene resin, polyester, etc. or a mixture of them. The '719 patent also discloses the method of forming films by electric field spraying (electrostatic spinning).

The US patent application publication number US-2012/0232224 A1 ("the '224 patent application") discloses a fibrous formed article having hydrophilicity property which contains a hydrophobic polymer and amphiphilic molecules and has an average fiber diameter of 0.05 to 50 μm. The method of the '224 patent application is achieved by electric field spinning. The dichotomy molecules disclosed in the '224 patent application are separated on the fiber surface.

However, the prior-art methods failed to provide an effective bandage in physiological wound healing which includes the following features: (a) providing scaffolding for granulation, re-epithelialization, and tissue formation, (b) providing hydrophilicity and non-adherence to avoid further damage on removal, (c) providing antimicrobial materials to better the healing process, and (d) preventing outside materials from infecting the wounds.

Therefore, what is needed is a medical dressing article and a method of fabricating the same that are effective in physiological wound healing.

What is needed is a method of manufacturing a medical dressing article that bind to the wound tissues and deliver antibiotic materials to the wound.

What is needed is a medical dressing article that provides scaffolding materials for granulation, re-epithelialization, and tissue formation.

What is needed is a medical dressing article that provides hydrophilicity and non-adherence to avoid further pain and tissue damage when the article is removed.

The present invention provides solutions to the above problems and meets the long-felt needs in new medical materials and the medical wound dressings.

SUMMARY OF THE INVENTION

Accordingly, the object of the present invention is to provide a medical dressing article that supports wound treatment, absorbs exudates from wounds, being non-adherent to avoids tears and damage when the article is removed, and providing antibacterial materials to wound; the medical dressing article including:

(i) at least one first layer made of polycaprolactone (PCL) where the diameter of the fiber is between 0.5 μm to 2.9 μm;

(ii) at least one second layer of fiber including a mixture of polycaprolactone (PCL) and poloxamer (POX), in which the diameter of the fiber is between 0.1 μm to 4 μm;

(iii) at least a third layer contains a mixture of gelatin and silver nitrate (AgNO3) is covered on the second layer.

Another object of the present invention is to provide a medical dressing article and a method of fabricating the same that are effective in physiological wound healing.

Yet an object of the present invention is to provide a method of manufacturing a medical dressing article that binds to the wound tissues and deliver antibiotic materials thereto.

An object of the present invention is to provide a medical dressing article that provides scaffolding materials for granulation, re-epithelialization, and tissue formation.

An object of the present invention is to provide a medical dressing article that provides hydrophilicity and non-adherence to avoid pain and tissue damage on removal.

These and other advantages of the present invention will no doubt become obvious to those of ordinary skill in the art after having read the following detailed description of the preferred embodiments, which are illustrated in the various drawing figures.

BRIEF DESCRIPTION OF THE DRAWINGS

The accompanying drawings, which are incorporated in and form a part of this specification, illustrate embodiments of the invention and, together with the description, explain the principles of the invention.

FIG. 6 shows images of stained epidermal cells of burns on the skin treated by the medical dressing article of the present invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

As used herein, the term "medical dressing articles" refers to bandages, gauzes, band-aids, cloths, pads, plasters, tapes, or the likes designed to cover external wounds regardless of the forms such as gels, gelatins, unwoven cloths, etc.

Figure 1:
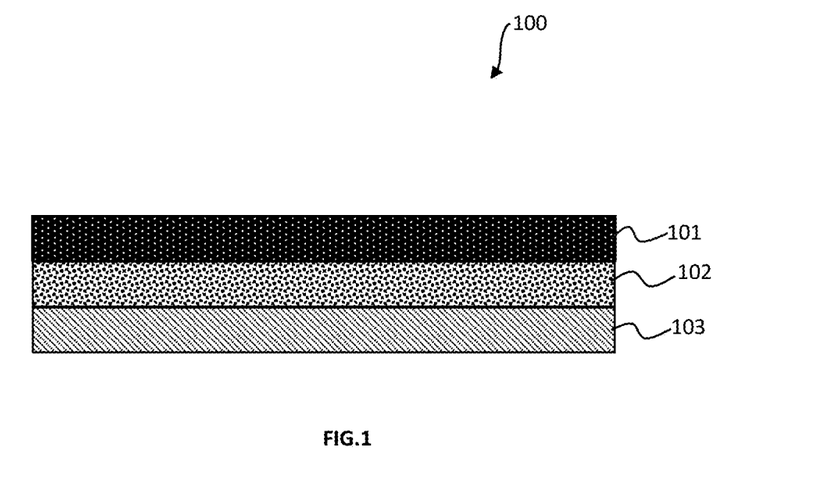
FIG. 1 shows different layer structure of a medical dressing article in accordance with an exemplary embodiment of the present invention.

Referring now to FIG. 1, a structure of a medical dressing article 100 in accordance with an exemplary embodiment of the present invention is illustrated. Medical dressing article 100 is comprised of (i) at least one first layer 101 made of polycaprolactone (PCL) where the cross-section area of the PCL fiber (fiber diameter) is between 0.5 μm to 2.9 μm; (ii) at least one second layer 102 including a mixture of polycaprolactone (PCL) and poloxamer (POX), in which fiber diameter is between 0.1 μm to 4 μm; (iii) at least a third layer 103 contains a mixture of gelatin and silver nitrate ($AgNO_3$) deposited directly on the wound area. First layer 101 is directly deposited on second layer 102 which is directly deposited on third layer 103. In this embodiment, third layer 103 containing antimicrobial materials such as gelatin and silver nitrate ($AgNO_3$) is arranged to make direct contact with the wound area.

According to a preferred embodiment of the present invention, the mass ratio between polycaprolactone (PCL) and poloxamer (POX) in second layer 102 ranges from 1:1 to 1:50.

According to a preferred embodiment of the present invention, the thickness of first layer 101 is between 0.1 mm to 2 mm, the diameter of the pores is about 7 μm to 20 μm.

According to a preferred embodiment of the present invention, second layer 102 is directly deposited on third layer 103 and the thickness of second layer 102 is between 0.02 mm to 0.3 mm.

According to a preferred embodiment of the present invention, third layer 103, deposited directly on second layer 102, further consisted of from 2 to 6 sub-layers. The thickness of each sub-layer ranges from 10 μm to 15 μm.

According to a preferred embodiment of the present invention, first layer 101 and second layer 102 are formed by the electric field spinning (ES) method (electrospinning).

According to a preferred embodiment of the present invention, third layer 103—directly deposited on second layer 102—is impregnated with a solution gelatin and $AgNO_3$ by immersion/overlay method. The gelatin has a concentration of 0.1% to 20%. The $AgNO_3$ has a concentration of 0.1% to 5%. The volume ratio between gelatin and $AgNO_3$ is from 1:1 to 50:1.

Figure 2:
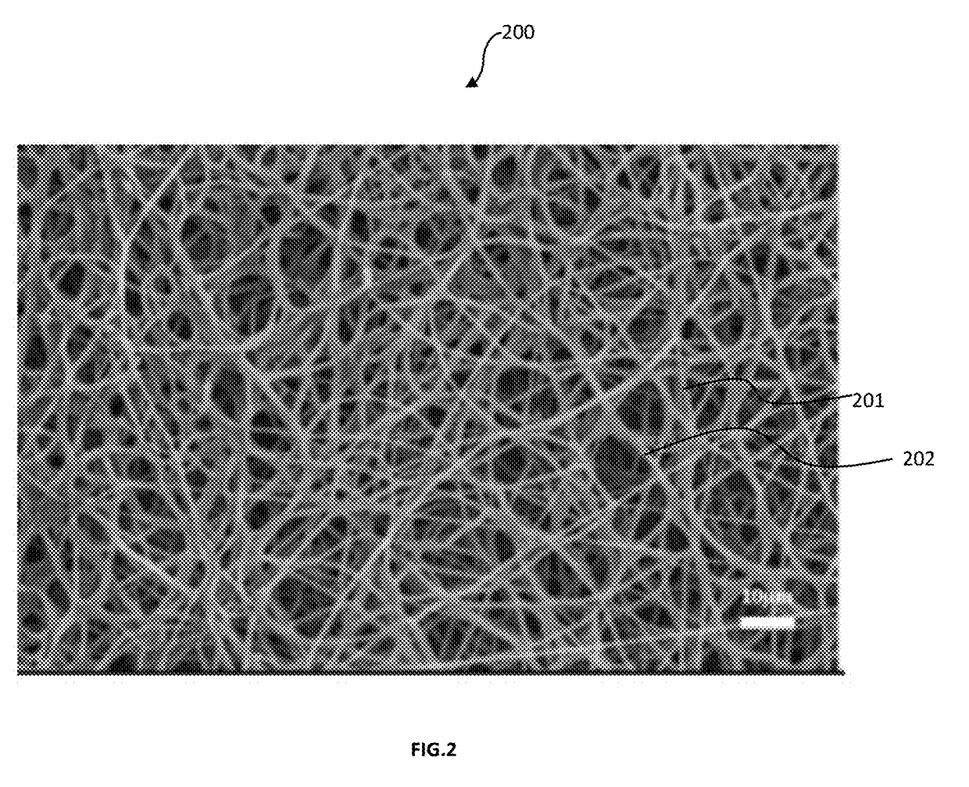
FIG. 2 presents a SEM images showing the fibrous structure of the medical dressing article in accordance with an exemplary embodiment of the present invention.

Referring next to FIG. 2, a SEM photo 200 of medical dressing article 100 in accordance with an exemplary embodiment of the present invention is illustrated. SEM photo 200 shows PCL fibers 201 of first layer 101 in which the fiber diameter of is in size ranges from 0.5 μm to 2.9 μm. Polycaprolacton and poloxamer fibers (PCL and POX fibers) 202 of second layer 102 are in the range of 0.1 μm to 4 μm, which is larger than PCL fiber 201 as shown in FIG. 2. At the intersection, PLC and POX fibers 202 and PCL fiber 201 are alternating and weaved together.

Figure 3:
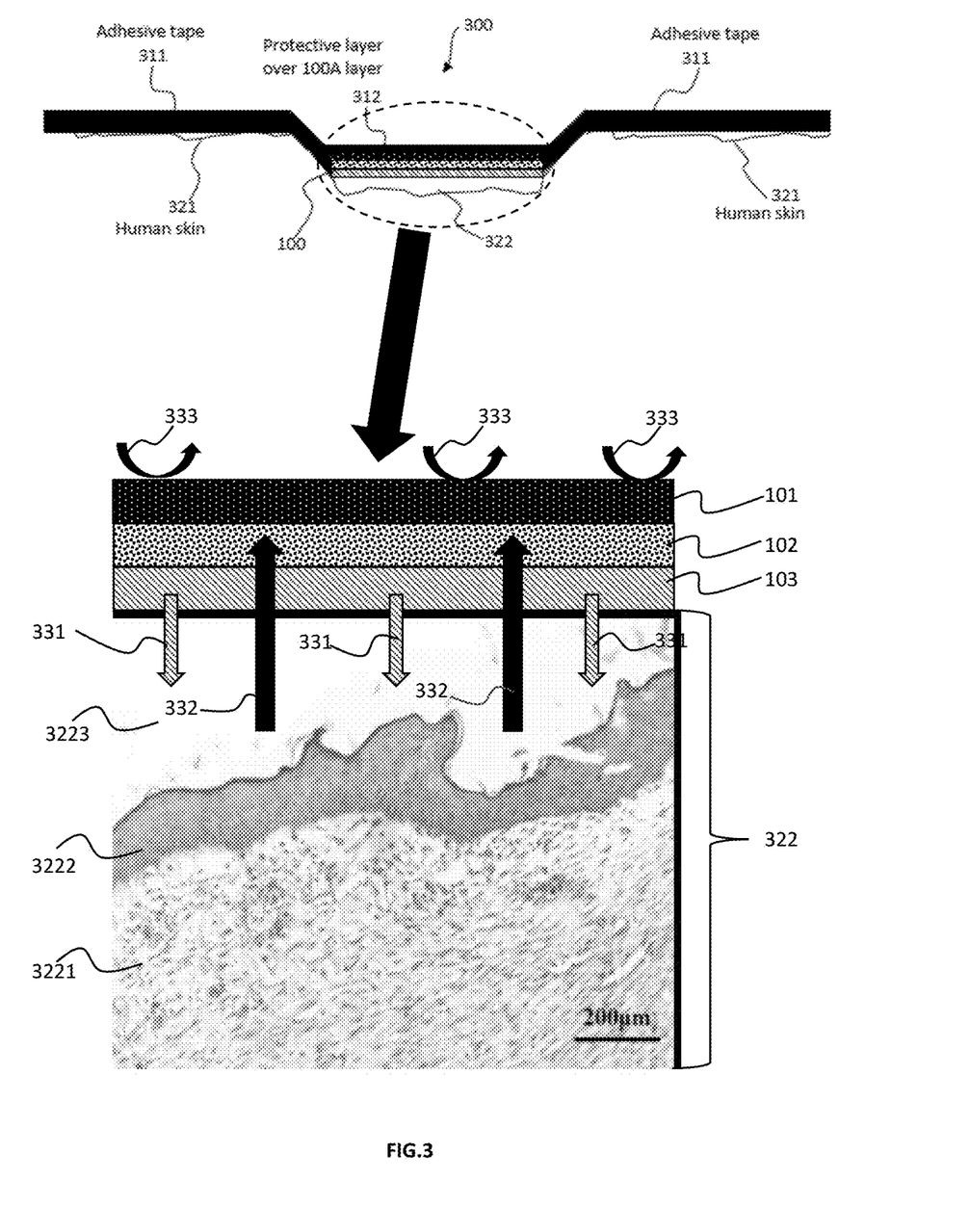
FIG. 3 illustrates a lateral view showing the operations of the medical dressing article in accordance with an exemplary embodiment of the present invention.

Referring to FIG. 3, a perspective diagram 300 explaining the operation of medical dressing article 100 on a wound is illustrated. Medical dressing article 100 is applied to a wound 322 in which third layer 103 containing gelatin and $AgNO_3$ are allowed to make direct contact with an epidermis layer 3223 of wound 322. At the same time, second layer 102 containing PCL and POX would deliver gelatin and $AgNO_3$ into wound area 322 according to a first direction 331. At the same time, second layer 102 draws excess exudates from wound 322 in a second direction 332, keeping wound 322 moist. With the fiber architecture of the second layer 102 as described, POX component in the PCL and POX fiber 202 has the effects of: (1) releasing active ingredients such as gelatin and $AgNO_3$ to wound area 322; (2) Drawing excess exudates from wound 322 that maintains optimal moisture inside wound area 322; and (3) providing extra cellular matrix (ECM) scaffolding for granulation, tissue formation, and re-epithelialization. In many embodiments of the present invention, in medical dressing article 100, second layer 102 naturally adheres to wound 322 without the need of additional adhesives. However, in some embodiments of the present invention, medical dressing article 100 is protected by a protective layer 312 which includes adhesive tapes 311. Adhesive tapes 311 are often used to keep medical dressing article 100 in place relative to wound area 322. Adhesive tapes 311 are useful in case the wounds are located in difficult areas on human body such as joints. Meanwhile, PCL fibers 201 in second layer 102 or first layer 103 is hydrophobic. They prevent contaminants and liquid containing bacteria or fluids from entering and infecting wound area 322. As shown in FIG. 3, on hydrophobic side of first layer 101, water carrying contaminants and bacteria are rejected in a third direction 333, prevented from entering and infecting wound area 322.

As disclosed in FIG. 1 to FIG. 3, medical dressing article 100 of the present invention achieves the following objectives:

(1) high humidity at the wound area 322 while removing excess exudates due to third layer 103 contacting wound area 322.

(2) Free of particles and toxic contaminants due to first layer 101 arranged on top in opposition to wound area 322 and second layer 102 arranged in the middle which is amphoteric or zwitterionic.

(3) Non-toxic and non-allergenic due to the materials selected such as gelatin, silver nitrate (AgNO₃), PCL, and POX, which are all biocompatible to human.

(4) Capable of protecting wound from further trauma due to the disclosed structure disclosed above.

(5) can be removed without causing trauma to the wound due to the optimal moisture at wound area 322 due to the function of second layer 102;

(6) Impermeable to harmful bacteria due to first layer 101 and second layer 102.

(7) Thermally insulating due to the properties of PCL in first layer 101 and POX and PCL in second layer 102.

(8) Allowing exchanging of air (breathable) due to the fiber diameters and thickness of first layer 101 and second layer 102.

(9) Requiring infrequent changes because of the optimal moisture and the tensile strength of the selected materials, fiber diameters, thickness, and structural arrangement, e.g., PCL, and PCL mixed with POX.

(10) cost effective since the selected materials are not expensive to purchase and/or manufacture.

Figure 4:
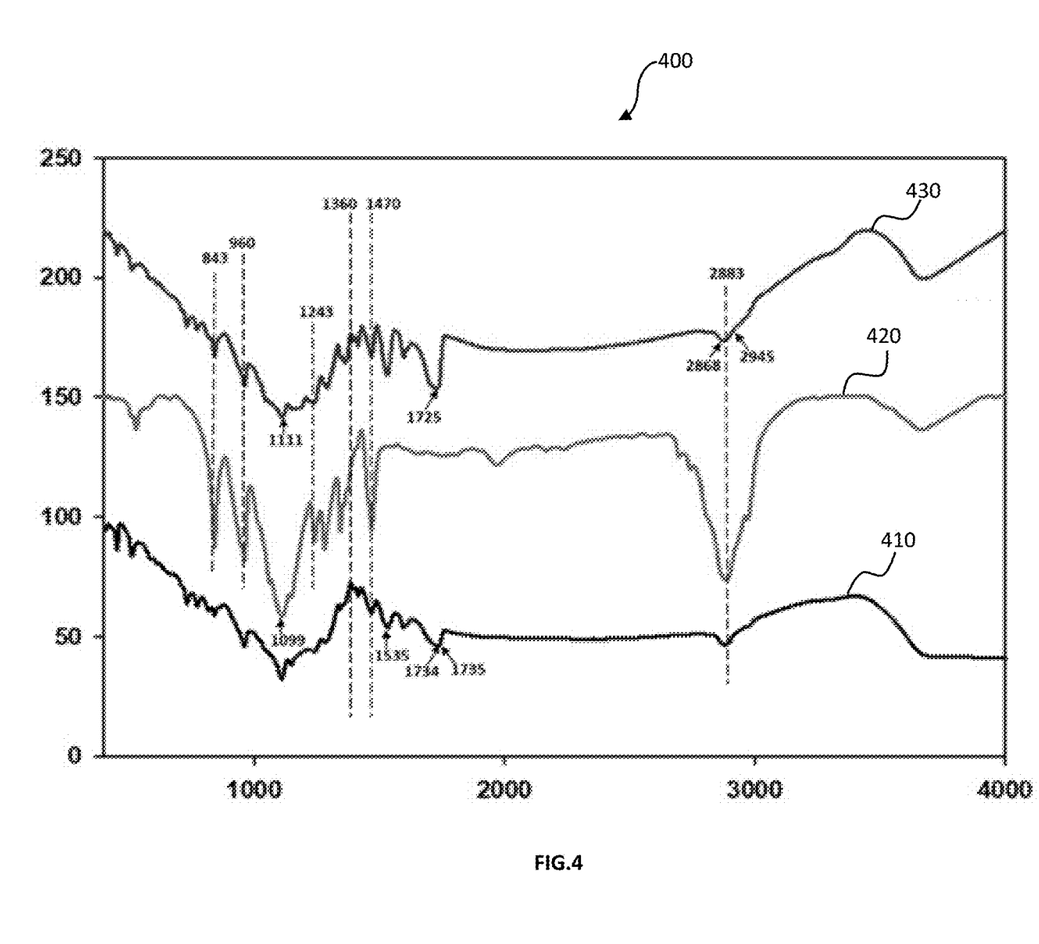
FIG. 4 is a Fourier transform infrared spectroscopy (FT-IS) chart of the medical dressing article in accordance with an exemplary embodiment of the present invention.

To evaluate the effectiveness of second layer 102 in combination with first layer 101 in the manner described above in FIG. 1 and FIG. 2, the Fourier transform infrared spectroscopy method known as the Fourier Transform infrared Spectroscopy (FTIR) is used to evaluate medical dressing article 100. Referring now to FIG. 4, a FTIR graph 400 of medical dressing article 100 is shown. According to FIG. 4, a spectrum 410 of polycaprolacton (PCL) film sample, the osteoarthritis of C=O belongs to the carbonyl ester group in PCL shown at 1,734 cm⁻¹. In addition, characteristic signals of PCL are also shown in the spectrum at 2,945 cm⁻¹ (d asymmetric stretch motor of —C—H), 2,883 cm⁻¹ (d symmetric tensile motor of —C—H) and 1,725 cm⁻¹ (pull of —C=O) shown in spectrum 430 of medical dressing article 100. On the other hand, the peaks at 960 and 843 cm⁻¹ correspond to the symmetric oscillation of the C—O—C link of the POX film sample shown in the 430 spectrum. The peaks in the area from 1,360 to 1,470 cm⁻¹ represent the signal coupling of the bending oscillations of C—H. The deformation oscillation of O—C—H and C—O—H of POX is shown in spectrum 420. The existence of POX in medical dressing article 100 is confirmed by a peak of 2,883 cm⁻¹ (d CH2 extension motor), 1,243 cm⁻¹ and 1,099 cm⁻¹ (elastic tensile labor of C—O—C) shown in spectrum 430. The intense oscillation of group C—O—C in POX at 1,099 cm⁻¹ and 1,111 cm⁻¹ shows that the combination of PCL and POX has been successful. Besides, the appearance of the peak 2,945 cm⁻¹ is shown in the spectrum 430 (d the stretchy labor of C—H in PCL) and 2868 cm⁻¹ (d the elongated labor of C—H in POX) also contributes to the alignment of functional groups of component polymers in PCL and POX.

Figures 5A, 5B:
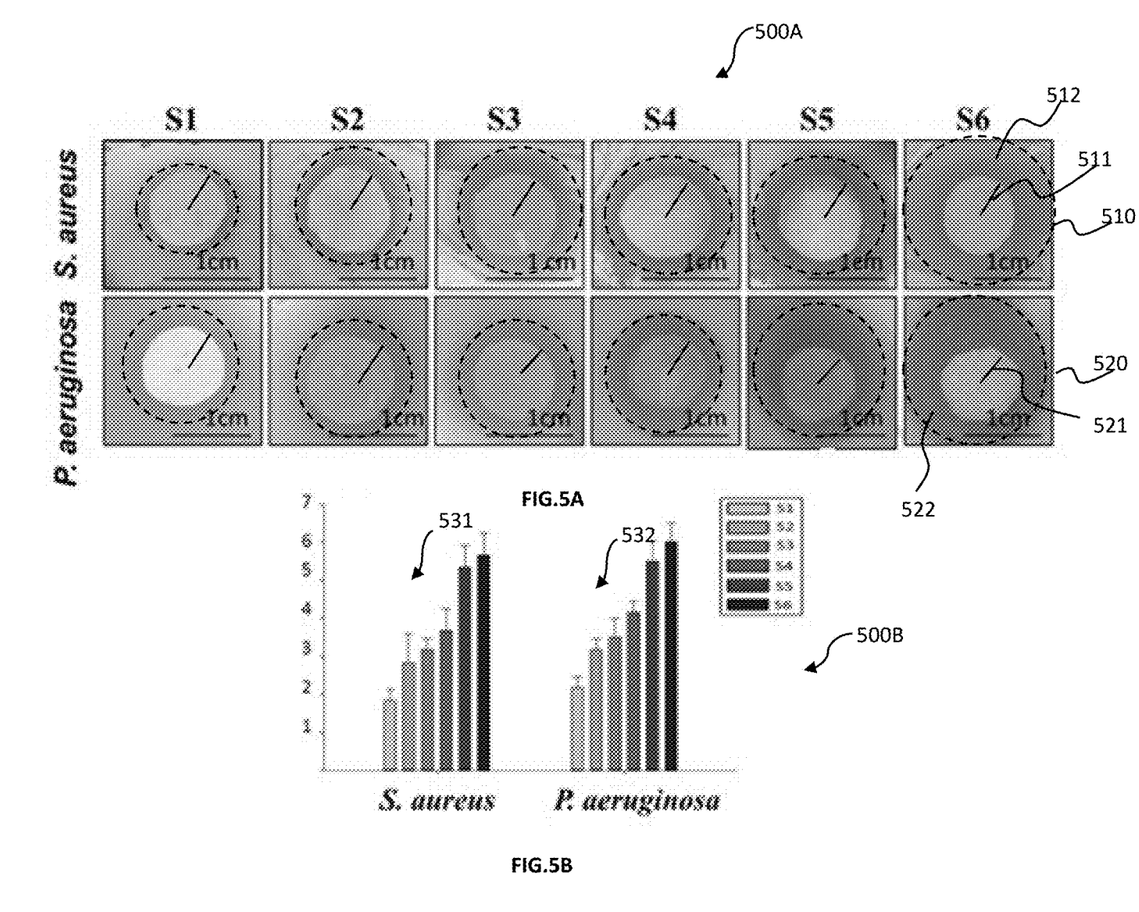
FIG. 5A exhibits antibacterial activities on jelly plates in accordance with an exemplary embodiment of the present invention.
FIG. 5B shows the antibacterial chart for *S. aureus* and *P. aeruginosa* bacteria in accordance with an exemplary embodiment of the present invention.

Next referring to FIG. 5A-FIG. 5B, different ways to convey the results of the antibacterial tests on gram-negative bacteria (*P. aeruginosa*) and gram positive bacteria (*S. aureus*) are shown. More particularly, diameter of inhibition zone (DIZ) results 500A of antibacterial tests including DIZ results 501 against *S. aureus* bacteria and DIZ results 502 against *P. aeruginosa* bacteria are shown. The diameter of inhibition zone (DIZ) shows the maximum distance that a bacteria can grow (or expand) against an antibacterial material such as gelatin and AgNO₃ of the present invention. The dark shadows 511 and 522 in DIZ results 501 and 502 respectively indicate the inhibition diameters or the effectiveness of an antibacterial material against the advancement of a particular bacteria represented by diameters 511 and 521 of *S. aureus* bacteria and of *P. aeruginosa* bacteria respectively. In the present test, S1 to S6 represent the number of sub-layers containing gelatin and AgNO₃ in third layer 103 from one layer S1 to six layers S6 respectively.

In DIZ results 501, *S. aureus* is a gram-positive bacterium, commonly found in the skin, nose and respiratory system. *S. aureus* bacteria can cause many diseases including skin infections and post-operative wounds and resistance to antibiotics were tested. Similarly, in DIZ results 502, *P. aeruginosa* bacteria, a common gram-negative bacteria, bacterial rod-shaped in soil, water, skin flora, also found on medical devices (e.g., urinary catheter) were tested. *P. aeruginosa* bacteria is commonly found in hospitals. Infections caused by *P. aeruginosa* are difficult to treat due to resistance to many antibiotics. Previous research results show that the smallest silver concentration is from 1 μg/ml to 2 μg/ml is sufficient to inhibit bacterial growth or achieve bactericidal effects. In the same manner, FIG. 5B shows bar graphs 500B of DIZ results against the same bacteria in a bar graph 511 against *S. aureus* bacteria in the horizontal axis and a bar graph 512 against *P. aeruginosa* bacteria also in the horizontal axis. The vertical axes of both graphs 511 and 512 represent the number of sub-layers in third layers 103.

Continuing with FIG. 5A and FIG. 5B, the results 500A and 500B show that all pathogens are significantly inhibited depending on the number of sub-layers, the more the sub-layers, the larger the DIZ and thus signifying the antibacterial strength increase. Specifically, according to the results of the *P. aeruginosa* antibacterial activity test for S1 was 2.2 mm, S2 was 3.2 mm, S3 was 3.5 mm, S4 was 4.2 mm, S5 is 5.5 mm and S6 is 5.8 mm; and *S. aureus* for S1 is 2 mm, S2 is 3 mm, S3 is 3.3 mm, S4 is 3.9 mm, S5 is 5.4 mm and S6 is 5.6 mm.

Figure 6:
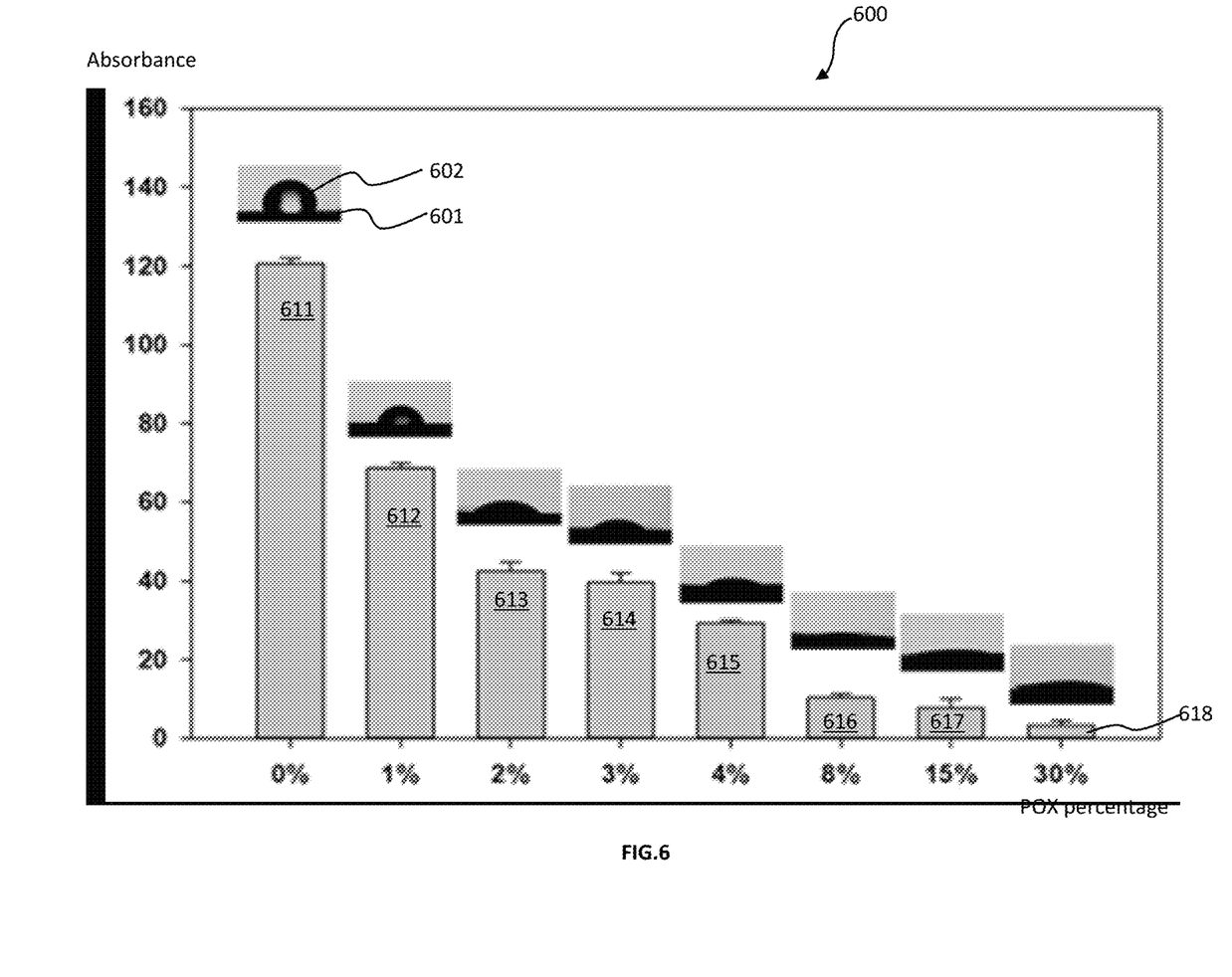
FIG. 6 shows a chart of different hydrophilicity strengths depending on the mass of POX added to the polycaprolactone (PCL) that supports the medical dressing article in accordance with various embodiments of the present invention.

Next referring to FIG. 6, a graph 600 of liquid absorbency (hydrophilicity) versus mass percentage (%) of poloxamer (POX) material added to medical dressing article 100 of the present invention is illustrated. The angular measurement methods were used to assess the effect of POX on a polycaprolacton (PCL) fiber surface 601 and also the hydrophilic properties of medical dressing article 100. The water exposure angle has decreased significantly even with the smallest POX concentration 612 of 1% blended in PCL fibers compared to pure PCL films 611. The water contact angle on PCL fiber surface 601 is virtually unchanged, while water droplets 602 gradually flattened or absorbed into PCL fiber surface 601 have a POX concentration of 1% to 30% represented by 612 to 618 respectively. Graph 600 shows that when the increased POX content from 612 to 618 increases the water permeability of medical dressing article 100. As shown in graph 611, PCL fiber surface 601 is impermeable to water droplet 602. At the other end, PCL fiber surface 601 totally absorbs water droplet 602 that they are indistinguishably flat surface. This makes hydrophobic PCL membranes super hydrophilic when mixed with POX. In addition, medical dressing article 100 also has autolytic debridement capacity with an average steam rate index of 3,554±381 g/m²/24 hours. This autolytic debridement capacity prevents the wound from falling into a vicious cycle of healing and back to infection and inflammation and healing because of foreign particles and bacteria.

Figure 7A:
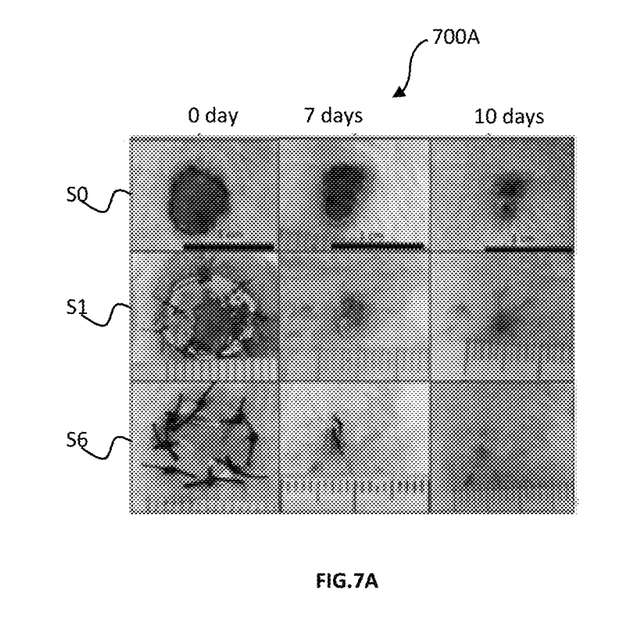
FIG. 7A shows the effective test results of wound healing on rats of the medical dressing articles in accordance with various embodiments of the present invention.
Figure 7B:
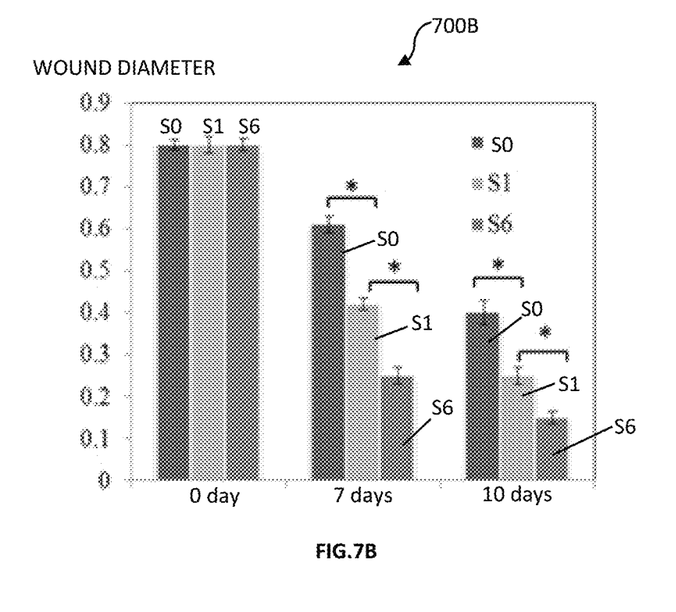
FIG. 7B shows a bar graph of wound healing efficacy in term of wound diameters of different wound dressing articles in accordance with various embodiments of the present invention.

Next, referring to FIG. 7A-FIG. 7B, wound treatment performance tests without and medical dressing article 100 of the present invention on wounds of laboratory rats are presented. Photos 700A showing S0 of control wound (without application of medical dressing article 100) after 0 day, 7 days, and 10 days. Photos S1 of wound treated with medical dressing article 100 with one sub-layer in third layer 103 after 0 day, 7 days, and 10 days. Photos S6 of wound treated with medical dressing article 100 with six sub-layers in third layer 103 after 0 day, 7 days, and 10 days respectively. Graph 700A shows that wound without any treatment, referred to as S0, was not completely healed after 10 days because it was open to the contamination of the environment. Graph 700A also shows that after covering the wound with (a) medical dressing article 100 having one sub-layer of gelatin mixture and $AgNO_3$, referred to as S1, was rapidly dried up and stuck to the wound surface; while (b) medical dressing article 100 having six sub-layers of gelatin mixture and $AgNO_3$, referred to as S6, do not stick to the wound and healed the wound nicely.

Now referring to FIG. 7B, a bar graph 700B plotting wound diameters of S0, S1 and S6 versus three different time periods of 0 day, days 7 and 10 is illustrated. According to bar graphs 700B, S6 healed the significantly faster than S1. On the $7^{th}$ day, the wound diameter decreased significantly from 8±0.12 mm to 6.1±0.2 mm for S0 I; from 8±0.12 mm to 4.2±0.2 mm for S1; and from 8±0.15 mm to 2.5±0.2 mm for S6. Comparison between 3 wounds, 8 mm wound closed about 1.9 mm; 3.8 mm and 5.5 mm respectively for S0, S1 and S6 cases. On the $10^{th}$, the wound diameter decreased significantly from 6.1±0.02 mm to 4±0.3 mm for S0; from 4.2±0.2 mm to 2.5±0.2 mm for S1; and from 2.5±0.2 mm to 1.5±0.15 mm for S6.

Figure 8:
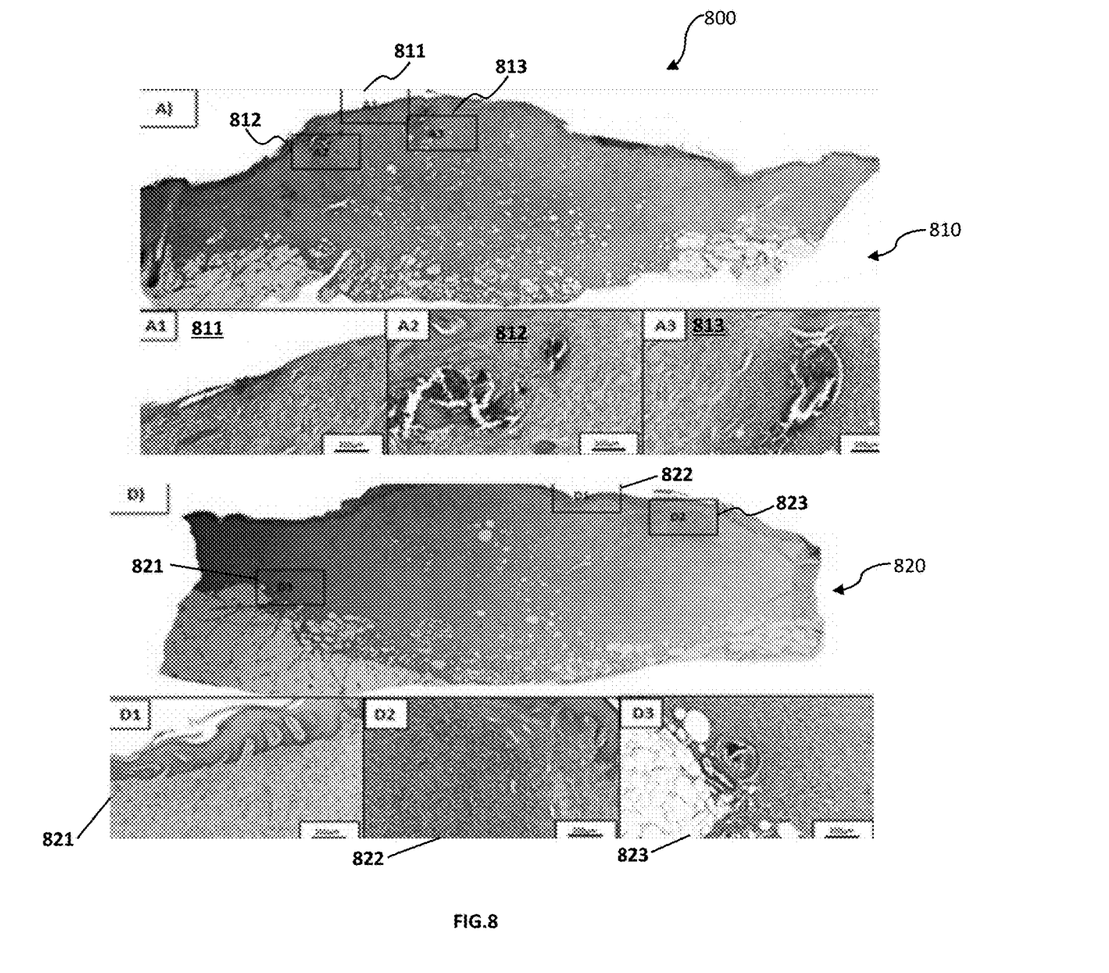

Now referring to FIG. 8, micrographs 800 showing the burn healing activities of a conventional bandages versus medical dressing article 100 of the present invention are illustrated. The results of the histological staining tests show that burn wounds treated with conventional bandages were almost impossible to support re-epithelialization shown in graphs 810. The histological examination of burn wounds were stained with hematoxylin and eosin. As shown in a graph 811, the epidermis layer increases in thickness due to the strong proliferation of fibroblast cells and the high density of inflamed cells. In addition, at the epidermis layer there are signs of necrosis shown in graph 812 and newly formed hair follicles are shown in a graph 813. Around the hair follicles were filled with lymphocytes and fibroblasts.

With the burn wound treated with medical dressing article 100 of the present invention, the epidermis layer was completely restructured shown in a graph 820. On the left side of the wound is a small area with many inflammatory cells such as neutrophils and invading cells shown in graph 821. There were no signs of infection or necrosis shown in a graph 822. In addition, the wound treated with an invention bandage shows the formation of the new blood vessels present in graph 823.

Figure 9:
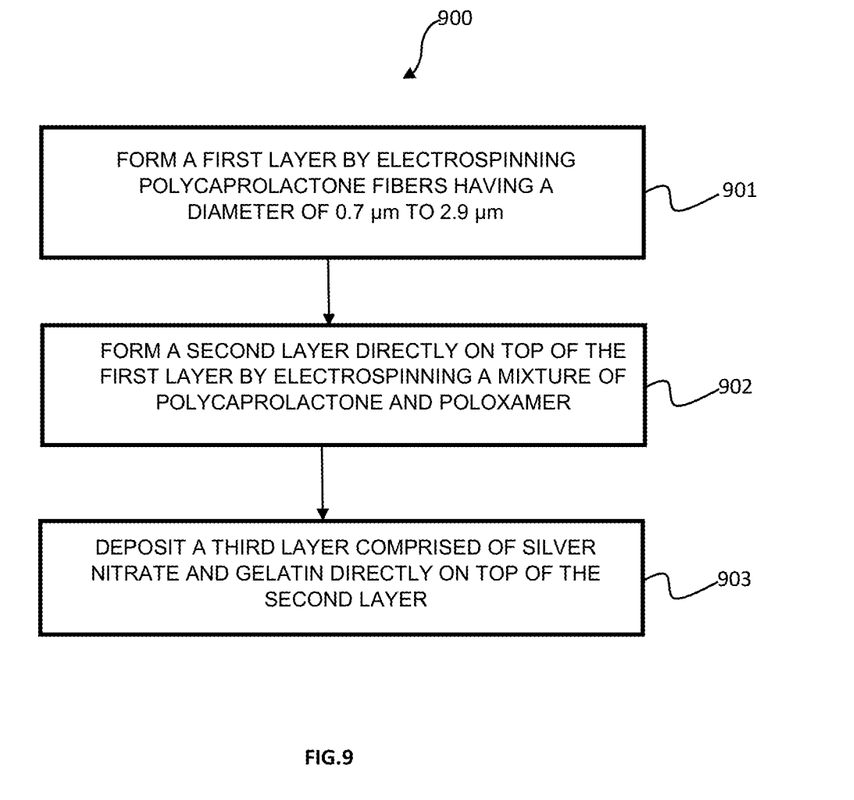
FIG. 9 shows a flow chart diagram of a method of fabricating the medical dressing article in accordance with various embodiments of the present invention.

Finally referring to FIG. 9, a flowchart of a method 900 of a medical dressing article in accordance with an exemplary embodiment of the present invention is illustrated.

At step 901, a first layer of polycaprolacton fibers (polycaprolactone-PCL) is formed. In many aspects of the present invention, the fiber diameter of the PCL fiber of step 901 is between 0.7 μm to 2.9 μm. Specifically, step 901 is realized by using electric field injection (electrospinning) solutions containing PCL concentrations of 10% to 15% in an electric field with a voltage supply ranging from 8 KV to 20 kV. PCL solution is prepared by dissolving PCL into the acetone solvent, then stirring for 12 hours at 50° C. until a homogeneous mixture is reached. This PCL solution is fed into a 12 centimeter diameter syringe. The syringe is then installed on the electric camcorder and sprayed with a power source from 8 kV to 20 kV. The fiber collection form is established by giving the horizontal collection roll by injection pump. The PCL solution is ejected from the pump system at a flow rate of 1 ml/hours until the thickness of the first layer is in the range of 0.1 mm to 2 mm.

Next at step 902, a second layer is deposited directly on the first layer. In many aspects of the present invention, the second layer is made of fibers consisting of a mixture of solutions containing PCL and POX, in which the fiber diameter is in the range of 0.1 μm to 4 μm. Specifically, fibers including PCL and POX are generated by electric field injection (electrospinning) a mixture of solutions containing PCL and POX from 10% to 15% in electric fields with a supply voltage from 15 kV to 20 KV. The mass ratio between polycaprolacton (PCL) and poloxamer (POX) ranges from 1:1 to 1:50. This mixture is sprayed using the voltage supply of 15 kV to 20 kV by setting the horizontal injection by injection pump at a flow rate of 1 ml/hour. The thickness of the second layer is between 0.02 mm to 0.3 mm.

Finally, at step 903, a third layer containing gelatin and $AgNO_3$ mixture is deposited directly on the first and second layers. Step 903 is realized by immersion of the second layer in a solution containing gelatin and $AgNO_3$ mixture in 30 minutes. In this mixture, gelatin has a concentration of 0.1% to 20% and $AgNO_3$ has a concentration of 0.1% to 5%, and the volume ratio between gelatin and $AgNO_3$ from 1:1 to 20:1. First, the gelatin solution is prepared by dissolving gelatin in distilled water and stirring at 400 rpm at 40° C. for 1 hour. Then add the prepared $AgNO_3$ solution and stir at room temperature for 10 minutes. The mixture is then exposed to ultraviolet light with a fluorescent lighting device within 1 hour and a mixture of gelatin and $AgNO_3$ solution is obtained. The third layer is covered with a second layer between 2 layers to 6 layers, the thickness of each layer is between 10 μm to 15 μm.

EXAMPLES

Example 1: Fabricating Medical Dressing Articles to Support Wound Treatment with a Mixed Coating of Gelatin and $AgNO_3$ Referring back to FIG. 1, first layer 101 is formed from polycaprolacton fiber (polycaprolactone—PCL), a 15% PCL solution is prepared by dissolving 1.5 grams of PCL into 8.5 grams of acetone solvent, then stir for 12 hours at 50° C. until a homogeneous mixture is reached. This PCL solution is fed into a 12-centimeter diameter syringe, after which the syringe is inserted into the electric camcorder and sprayed with 15 kV power. PCL solution is ejected from the pump system at a flow rate of 1 ml/hour and first grade, in which the diameter of yarn is between 0.7 μm to 2.9 μm.

Next, depositing the second layer 102 onto first layer 101, in which second layer 102 is made up of fibers consisting of a mixture of solutions containing PCL and POX. Specifically, put 1 ml of POX into 9 ml of PCL solution to achieve a solution containing 10% of POX solution.

The mixture of this solution is then fed into a syringe with a diameter of 12 centimeters. The syringe is then installed on the electric camera and sprayed with 18 kV power supply. The mixture of PCL and POX solutions was ejected from the pump system at a flow rate of 1 ml to deposit second layer 102 directly on first layer 101. The fiber diameter of second layer is in the range of 0.1 µm to 4 µm.

Finally, third layer 103 containing a mixture of gelatin and AgNO$_3$ was deposited on second layer 102 to obtain medical dressing article 100. Specifically, a 3% gelatin solution was prepared by dissolving 0.3 grams of gelatin in 9.7 grams of distilled water and stirring at 400 rpm/minutes at 40° C. for 1 hour and obtained approximately 10 ml of gelatin solution. Next, 1 ml of prepared 1% AgNO$_3$ solution was added and stirred at room temperature for 10 minutes. Next, the mixture was exposed to ultraviolet light with a fluorescent lighting device within 1 hour. The mixture of gelatin and AgNO$_3$ solution was obtained. Then, first and second layers 101 and 102 were immersed into the mixture of gelatin and AgNO$_3$ solutions within 30 minutes to obtain medical dressing article 100.

Example 2: Fabricating the Medical Dressing Article with Three Gelatin and AgNO$_3$ Layers After the first experiment was completed, drying medical dressing article 100 mixed coating of gelatin and AgNO$_3$ for six hours. Then, soaking medical dressing article 100 into the mixture of gelatin and AgNO$_3$ solutions for 30 minutes to create a second sub-layer. Continuing to perform drying and coating of the same gelatin and AgNO$_3$ to obtain medical dressing article 100 with three sub-layers of gelatin mixed with AgNO$_3$.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

DESCRIPTION OF NUMERALS

100 Medical dressing article of the present invention
101 First layer of polycapralactone (PCL)
102 Second layer of PCL and poloxamer (POX)
103 third layer of a mixture of gelatin and AgNO$_3$
201 PCL fiber
202 PCL and POX fiber
300 medical dressing article with adhesive tapes
311 adhesive tapes (optional)
312 protective layer (optional)
321 human skin layer
322 wound area
3221 dermis layer
3222 epidermis layer
3223 polycaprotoner (PCL) impermeable layer
331 releasing direction of gelatin and AgNO$_3$
332 fluid absorption direction
333 fluid rejection direction
400 Fourier transform infrared spectroscopy spectrum
410 spectrum of PCL layer
420 spectrum of POX layer
430 spectrum of medical dressing article with three layers
500A diameter inhibition zone (DIZ) tests
500B bar graphs of DIZ tests
511 expansion diameter of S. aureus against article
512 inhibition zone of S. aureus
521 expansion diameter of P. aeruginosa against article
522 inhibition zone of P. aeruginosa
531 DIZ bar graph of S. aureus
532 DIZ bar graph of P. aeruginosa
600 POX hydrophilicity test
601 PCL and POX surface
602 water droplet
611 PCL control group
612 PCL with 1% POX
613 PCL with 2% POX
614 PCL with 3% POX
615 PCL with 4% POX
616 PCL with 8% POX
617 PCL with 15% POX
618 PCL with 30% POX
700 healing test against control group
800 histological examination against conventional bandage

What is claimed is:

1. A medical dressing article, comprising:
    a first layer comprised of polycaprocaptone fibers having a PCL fiber diameter between 0.5 µm to 2.9 µm;
    a second layer including a mixture of polycaprolactone and poloxamer fibers (PCL and POX fibers) wherein PCL and POX fiber diameters are between 0.1 µm to 4 µm; and
    a third layer further comprising a mixture of gelatin and silver nitrate (AgNO$_3$), wherein said third layer is configured to make direct contact with a wound, said second layer is directly deposited directly on said third layer, and said first layer is directly deposited on said second layer.

2. The medical dressing article of claim 1 wherein said first layer has a thickness between 0.1 mm to 2 mm.

3. The medical dressing article of claim 2 wherein a diameter of a pore (void space) between said PCL fiber in said first layer is between 7 µm to 20 µm.

4. The medical dressing article of claim 1 wherein said second layer has a thickness of 0.02 mm to 0.3 mm.

5. The medical dressing article of claim 1 wherein a ratio of said poloxamer (POX) fibers and said polycaprocaptone (PCL) fibers in said second layer is 15%.

6. The medical dressing article of claim 1 wherein a ratio of said poloxamer (POX) fibers and said polycaprocaptone (PCL) fibers in said second layer is 30%.

7. The medical dressing article of claim 1 wherein said third layer further comprises two to six sub-layers of gelatin and silver nitrate (AgNO$_3$).

8. The medical dressing article of claim 7 wherein a thickness of each of said sub-layers is between 10 µm to 15 µm.

9. The medical dressing article of claim 8 wherein said gelatin has a concentration of 0.1% to 20%.

10. The medical dressing article of claim 9 wherein said silver nitrate (AgNO$_3$) has a concentration of 0.1% to 5%.

11. The medical dressing article of claim 10 wherein a volume ratio between gelatin and AgNO$_3$ is from 1:1 to 50:1.

12. The medical dressing article of claim 1 wherein a mass ratio between said polycaprolactone and said poloxamer in said second layer ranges from 1:1 to 1:50.

13. A method of fabricating a medical dressing article, comprising:
    (i) forming a first layer of polycaprocaptone fibers having PCL fiber diameters are between 0.5 µm to 2.9 µm;
    (j) forming a second layer directly on said first layer, said second layer including a mixture of polycaprolactone and poloxamer fibers (PCL and POX fibers) wherein PCL and POX fiber diameters are between 0.1 µm to 4 µm; and (k) forming a third layer directly on said second layer, said third layer further comprising a mixture of gelatin and silver nitrate ($AgNO_3$).

14. The method of claim 13 wherein further comprising (iv) a protective layer directly on top of said first layer.

15. The method of claim 14 wherein said step (i) further comprises electrospinning said first layer at a voltage potential of 8 kV to 20 kV until said first layer has a thickness between 0.1 mm to 2 mm.

16. The method of claim 13 wherein said step (ii) further comprises electrospinning said second layer at a voltage potential of 8 kV to 20 kV said second layer has a thickness of 0.02 mm to 0.3 mm.

17. The method of claim 13 wherein a ratio of said poloxamer (POX) fibers and said polycaproctone (PCL) fibers in said second layer is 30%.

18. The method of claim 13 wherein said step (iii) further comprising forming said third layer that includes two to six sub-layers of gelatin and silver nitrate ($AgNO_3$).

19. The method of claim 18 wherein a thickness of each of said sub-layers is between 10 µm to 15 µm.

20. The method of claim 18 wherein said gelatin has a concentration of 0.1% to 20% and wherein said silver nitrate ($AgNO_3$) has a concentration of 0.1% to 5%.

* * * * *